United States Patent [19]
Fujino et al.

[11] 3,973,945
[45] Aug. 10, 1976

[54] PYRAN-2,4-DIONE DERIVATIVES

[75] Inventors: Akiharu Fujino, Zushi; Isao Iwataki, Odawara; Yoshihiko Hirono, Hiratsuka, all of Japan

[73] Assignee: Nippon Soda Company Ltd., Tokyo, Japan

[22] Filed: Nov. 25, 1974

[21] Appl. No.: 526,746

[30] Foreign Application Priority Data
Dec. 5, 1973  Japan.............................. 48-135274

[52] U.S. Cl.................................. 71/88; 260/343.5; 260/345.9; 204/158 R
[51] Int. Cl.².................... A01N 9/20; C07D 309/38
[58] Field of Search...................... 260/343.5; 71/88

[56] References Cited
FOREIGN PATENTS OR APPLICATIONS
7,305,083  10/1973  Netherlands..................... 260/343.5

*Primary Examiner*—Jane S. Myers
*Attorney, Agent, or Firm*—George B. Oujevolk

[57] ABSTRACT

A compound of the formula

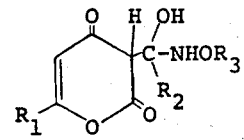

wherein $R_1$ and $R_2$ are alkyl having six or less carbon atoms, $R_3$ is selected from the group consisting of alkyl having six or less carbon atoms and alkenyl having six or less carbon atoms, with the proviso that $R_1$ and $R_2$ don't represent simultaneously methyl group;
are useful as selective herbicide.

6 Claims, 1 Drawing Figure

PYRAN-2,4-DIONE DERIVATIVES

DETAILED DESCRIPTION OF THE INVENTION

Figure 1:
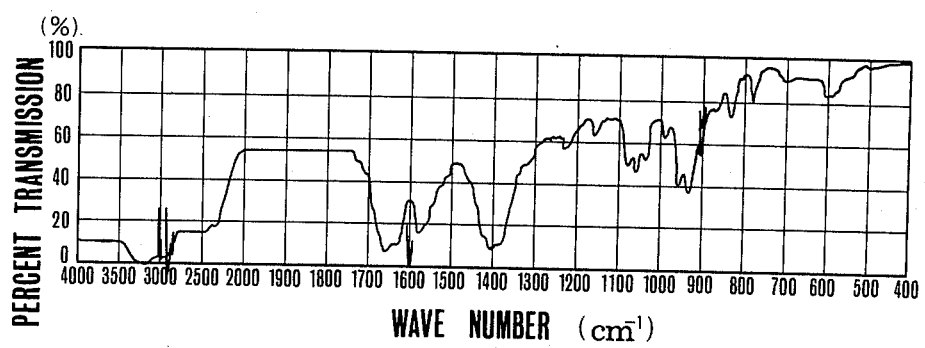

The present invention relates to novel compounds of 3,4-dihydro-2H-pyrane-2,4-diones, the process for the preparation thereof and their uses as herbicides having selective activity.

Further, this invention relates to herbicidal compositions containing one or more of novel compounds, and to the method of controlling weeds which comprises applying to plant or to soil the said compounds.

It is an object of the present invention to prepare new 3,4-dihydro-2H-pyrane-2,4-diones.

Another object is to provide an improved compositions and processes for killing undesired plants.

The inventors synthesized quite a few compound of 3,4-dihydro-2H-pyrane-2,4-dione derivatives and tested the biological activities the compounds.

As the result of the test, it has been discovered that the new and novel compounds of the present invention are particularly effective as herbicides.

The novel compounds of this invention are characterized by the following formula:

[I]

wherein $R_1$ and $R^2$ are alkyl having six or less carbon atoms, $R_3$ is selected from the group consisting of alkyl having six or less carbon atoms and alkenyl having six or less carbon atoms, with the proviso that $R_1$ and $R_2$ don't both represent a methyl group; however, the compounds of the present invention have the following three chemical formulae because of their tautomerism:

[I]    [II]

[III]

Preferred are those compounds where $R_1$ and $R_2$ are alkyl of 2 to 3 carbon atoms and $R_3$ is alkyl of 2 to 3 carbon atoms an allyl group. Particularly preferred because of its high order of herbicidal activity is: 3-(1-ethoxyamino-1-hydroxypropyl)-6-ethyl-3,4-dihydro-2H-pyrane-2,4-dione. But, those compounds were $R_1$ and $R_2$ both represent methyl don't have a superior herbicidal activity. The compounds of this invention can be prepared in accordance with the following equation:

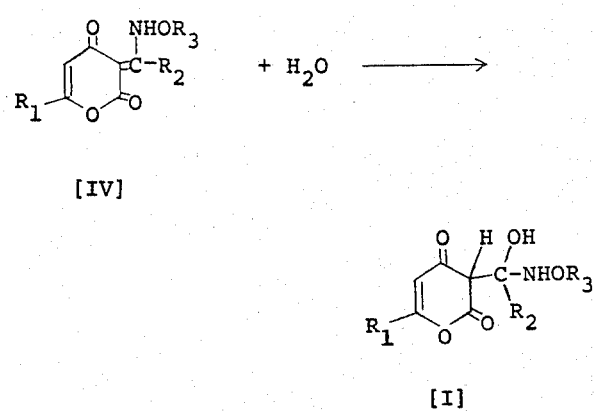

[IV]

[I]

wherein $R_1$, $R_2$ and $R_3$ are as previously defined.

In a practical method the compounds of this invention are prepared through the reaction of general formula [IV] with water under the irradiation with light.

The above reaction can be conducted both in an inert solvent and in the absence of a solvent, but preferably in an inert solvent. By using an inert solvent the compounds of this invention are obtained in high yield.

As an inert solvent, alcohol, acetone, ether, dioxane, chloroform, benzene and toluene, preferably acetone, are used. It is, in many cases, preferably to use the above solvent containing water of 1 to 10%, more preferably of 2 to 5%, as the reactant.

Ordinarily, temperatures from the range of 0°–100°C, and preferably 10° – 35°C, are satisfactorily employed for the above reaction and the reaction terminates between 0.5 and 60 hours, in several days in some case.

As the light irradiated in the above reaction, ultraviolet light is preferably used and high-pressure mercury arc is ordinarily used as ultraviolet source.

After the reaction has terminated, the crude product is isolated from the reaction mixture by filtration or by extraction with a solvent.

A chemical structure of the resulting purified compound can be positively identified by means of elementary analysis, NMR spectrum and IR spectrum.

It is also expected that the starting compound represented by the formula [IV] has the following three chemical formulae including formula [IV] because of its tautomerism.

[V]    [VI]

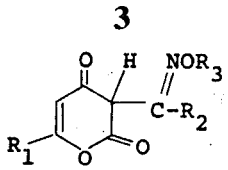

[VII]

The starting compound [IV] can be prepared in accordance with the following equation:

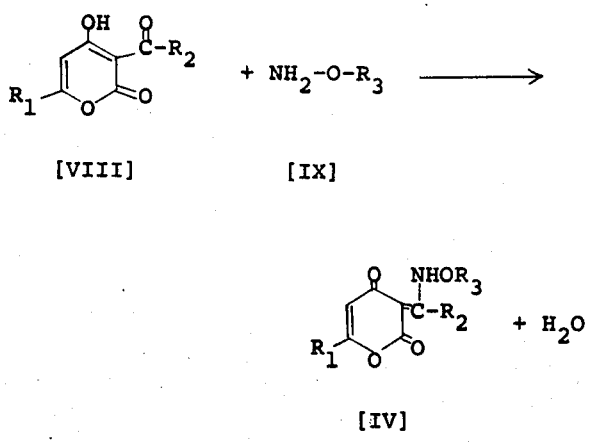

It is theoretically suggested according to the reaction mechanism that the compound of this invention may be formed as the intermediate in the process of above condensation reaction which implies the addition of formula [IX] and the fast elimination of a molecule of water.

In order to facilitate a clear understanding of the invention, the following preferred specific embodiments are described as illustrative and not as limiting the invention.

EXAMPLE 1

Preparation of 3-(1-ethoxyamino-1-hydroxypropyl)-6-ethyl-3,4-dhydro-2H-pyrane-2,4-dione 1.0g of 3-(1-ethoxyaminopropylidene)-6-ethyl-3,4-dihydro-2H-pyrane-2,4-dione (m.p. 56°–57°C) was dissolved in 50 ml of acetone containing 2% of water. After it was poured shallowly into the vessel having an area of (30 × 35) cm² and dried, it was allowed to stand for a week in the sunlight. 980mg of the crude product was obtained by the distillation of methanol after the precipitated crystal on the container was recovered by washing with methanol. The crude product was recrystallized three times from the mixture of ethanol and water, and 600 mg of 3-(1-ethoxyamino-1-hydroxypropyl)-6-ethyl-3,4-dihydro-2H-pyrane-2,4-dione having a melting point of 63° to 64°C as a white crystal was obtained. From the results of NMR spectrum this compound showed a multiplet of 9H intensity at $\delta 1.20$ ppm, a singlet of 1H intensity at $\delta 1.70$ ppm, two quartet of 2H intensity both at $\delta 2.50$ and $\delta 2.64$ ppm, a quartet of 2H intensity at $\delta 4.10$ ppm, a singlet of 1H intensity at $\delta 5.80$ ppm and a singlet of 1H intensity at $\delta 8.22$ ppm, and showed the maximum absorption at a wavelength 293 m$\mu$ ($\epsilon$=8300) in ethanol at the ultraviolet spectrum.

Elemental analysis-Calculated for $C_{12}H_{19}NO_5$(%):C56.03, H7.39, N5.45. Found(%):C56.00, H7.69, N5.37.

EXAMPLE 2.

Preparation of 3-(1-allyloxyamino-1-hydroxypropyl)-6-ethyl-3,4-dihydro-2H-pyrane-2,4-dione 1.0 g of 3-(1-allyloxyaminopropylidene)-6-ethyl-3,4-dihydro-2H-pyrane-2,4-dione ($N_D^{26.5}$:1.5389) was dissolved in 50ml of acetone containing 5% of water. After it was poured shallowly into the vessel having an area of (30×35)cm², it was allowed to stand for a day in the sunlight. 630mg of the crude product was obtained by the distillation of methanol after the precipitated crystal on the container was recovered by washing with methanol. The crude product was recrystallized three times from the mixture of ethanol and water and 300mg of 3-(1-allyloxyamino-1-hydroxypropyl)-6-ethyl-3,4-dihydro-2H-pyrane-2,4-dione having a melting point of 62.5° to 64°C as a white crystal was obtained.

EXAMPLE 3

Preparation of 3-(1-ethoxyamino-1-hydroxypropyl)-6-ethyl-3,4-dihydro-2H-pyrane-2,4-dione After 1g of 3-(1-ethoxyaminopropylidene)-6-ethyl-3,4-dihydro-2H-pyrane-2,4-dione was dissolved in 50ml of acetone containing 5% of water, it was irradiated with high-pressure mercury arc for a day. Chloroform was added to the residue after the distillation of acetone and the insoluble crystal was obtained by filtration of chloroform solution containing the residue. The crude product was recrystallized from the mixture of benzene and petroleum ether, and thereby 0.6g of 3-(1-ethoxyamino-1-hydroxypropyl)-6-ethyl-3,4-dihydro-2H-pyrane-2,4-dione having a melting point of 63° to 64°C as a white plate was obtained.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (*Poa annua L.*); water foxtail (*Alopecurus aequalis* Sobol), large crabgrass (*Digitaria adscendens* Henr.), green foxtail (*Seturia viridis* Beauv), wild oat (*Avena fatua* L) etc. and they hardly injure broad leaf crops such as adzuki bean (*Phaseolus angularis* W. F. Wight) and soy bean (*Glycine max* Merrill) and sugar beets (*Beta vulgaris* L.) which easily suffer phyto-toxicity. Namely, the compounds of the invention are the selective herbicide.

It is already known that 4-hydroxy-6-methyl-$\alpha$-pyrone derivatives has herbicidal properties as shown in Japanese Patent Publication No. 16916/1971.

But in order to destroy completely the said grass weeds, a large amount of the above herbicidal chemical is required and this is one drawback for these herbicidal compound.

In other words, according to the descriptions of the above mentioned prior art and the results of additional experiments by the inventors, a chemical amount containing 500g of effective ingredient, in proportion to 10 are (a metric unit which is 100 square meters) of area is able to give an expected effect in the case of employing it practically, but another chemical amount containing 250g of effective ingredient, in proportion to 10 are of area is not able to cause grass weeds to wither to death, in the other words, it cannot give a good herbicidal effect.

In employing the compound of the present invention as a herbicide, a chemical amount containing 250g of effective component, as a matter of course, further a chemical amount containing 125g or less of effective ingredient, in proportion to 10 are of area, in compliance with the same treating method of conventional herbicide exhibits a strong herbicidal effect and thereby prevention and extermination of weeds can be expected.

In case of foliar treatment using the compounds of the present invention, even the same amount of chemical which kills barnyard grass of grass weeds causes no damages to broadleaf plants such as the radish (*Raphanus sativus* L.), soy bean, garden pea (*Pisum sativum* L.), spinach (*Spinacia oleracea* L.) sugar beets and carrot (*Dancus carota* L.) at all, and in case of soil treatment before germination, even the same amount of chemicals which prevents large crab-grass germinating causes no damages to seeds of broad leaf plants.

As mentioned above, protection to the broadleaf crop against phytotoxicity of the herbicide is extremely high and as to its application, e.g., its applicable time, its applying location and its applying concentration, it has a very broad extent and it can be used to a wider extent.

It is another advantage of the present invention that a residual toxicity in the soil or the plant and an acute toxicity for warm blooded animals and fish need not be feared.

The compounds of this invention can be applied directly to the soil as a pre-emergence treatment or to plant foliage as a post-emergence treatment, or they can be mixed intimately with the soil, preferably pre-emergence treatment to the soil, and may be applied to soil or plant foliar at rates of 50–1000g per 10 are, preferably about 100g per 10 are.

The method of the present invention comprehends the employment of a liquid or solid composition containing one or more of the present compounds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent are added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicides it is recommended that the compounds of the present invention be applied admixed with urea derivatives such as 3-(3,4-dichlorophenyl)-1-methoxy-1-methyl-urea, or N-(3,4-dichlorophenyl)N', N'-dimethylurea, triazine derivatives such as 2-chloro-4-ethylamino-6-isopropylamino-s-triazine, or 2-chloro-4,6-bis(ethylamino)-s-triazine and amide derivatives such as N-1-naphthyl-phthalamic acid.

The concentrations of the active ingredients in the herbicidal composition of this invention vary according to type of formulation, and they are, for example, used in a range of 5 – 80 weight percent, preferably 10 – 60 weight percent, in wettable powder, 5 – 70 weight percent, preferably 20 – 60 weight percent, in emulsifiable concentrates, and 0.5 – 30 weight percent, preferably 1 – 10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulation is directly used for the soil treatment or the foliar treatment.

The non-limiting examples for the herbicidal composition are illustrated as follows:

EXAMPLE 4

| Wettabl Powder | Parts by weight |
| --- | --- |
| Compound of Example 1 | 50 |
| Diatomaceous earth | 21 |
| Sodium alkylsulfate | 8 |
| Talc | 21 |

These are mixed homogeneously and reduced to fine particles. Consequently, a wettable powder containing 50% of active ingredient is obtained. In practical use, it is diluted to a certain concentration with water and is sprayed as a suspension.

EXAMPLE 5

| Emulsifiable Concentrate | Parts by weight |
| --- | --- |
| Compound of Example 1 | 40 |
| Xylene | 35 |
| Dimethylformamide | 15 |
| Polyoxyethylene phenylether | 10 |

These are mixed and dissolved.

Consequently, an emulsifiable concentrate containing 40% of the active ingredient is obtained. In practical use, it is diluted to certain concentration with water and then is sprayed as an emulsion.

Example 6

| Dust Formulation | Parts by weight |
| --- | --- |
| Compound of Example 2 | 7 |
| Talc | 35 |
| Bentonite | 16 |
| Clay | 35 |
| Sodium alkylsulfate | 7 |

These are mixed homogeneously and reduced to fine particles. Fine particles are made into granules having the diameter in the range of 0.5 — 1.0mm by granulator.

Consequently, dust formulation containing 7% of the active ingredient is obtained. In practical use it is directly applied.

The superior herbicidal effect of the novel compounds of this invention is clearly illustrated by the following tests.

TEST 1

Pre-emergence treatment (soil treatment in paddy condition)

About 60 seeds of barnyard grass were planted in a pot having 60 square centimeters and covered slightly with soil. Water was poured into the pot until the surface of the soil became wet.

10 ml of an aqueous emulsion prepared by diluting an emulsifiable concentrate with water to a specified concentration was sprayed on the pot. The pots were kept in a green house and water was added to the pots daily in order to keep the water level. Three weeks after spraying, the degrees of damage to the plant were observed and estimated by the values of 0 – 5 which have the following meanings:

0: no effect
1: partial plant slightly injured
2: plant slightly injured
3: plant moderately injured
4: plant severely injured
5: plant completely killed or no germination The results were shown in Table 1.

Table 1

| Test compound | Application rate (g/10 are) | | | |
|---|---|---|---|---|
| | 250 | 125 | 62.5 | 31.3 |
| Compound of Example 1 | 5 | 5 | 5 | 5 |
| Compound of Example 2 | 5 | 5 | 5 | 5 |
| Comparative compound 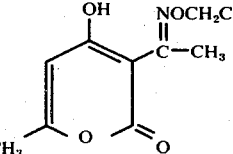 | 4 | 4 | 2 | 0 |
| Untreated | | | | 0 |

TEST 2

Post-emergence treatment foliar treatment in paddy condition)

About 50 seeds of barnyard grass were planted in a pot having 60 square centimeters and covered slightly with soil. Said pot was filled with water to about 3cm above the surface of the soil when the plant was grown to first leaf-stage.

An aqueous emulsion prepared by diluting an emulsifiable concentrate with water to a specified concentration was sprayed on the pot. The pots were kept in a green house and water was added to the pot daily in order to keep the water level. Two weeks after spraying, the degrees of damage to the test plant was observed and estimated by the values of 0 – 5 which have the same meanings as those of Test 1.

The results were shown in Table 2.

Table 2

| Test compound | Application rate (g/10 are) | | |
|---|---|---|---|
| | 125 | 62.5 | 31.3 |
| Compound of Example 1 | 5 | 5 | 5 |
| Compound of Example 2 | 5 | 5 | 4 |
| Comparative compound 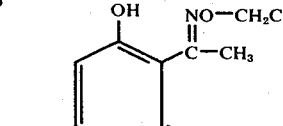 | 4 3 | 1 0 | 0 0 |
| Untreated | | | 0 |

TEST 3

Pre-emergence treatment

Seeds of large crab-grass were planted in a pot having 100 square centimeters. An aqueous emulsion prepared by diluting an emulsifiable concentrate with water to a specified concentration was sprayed on the surface of the soil before emergence. The pots were kept in a green house. 21 days after spraying, the degrees of damage to the test plants were observed and estimated by the value of 0 – 5 which have the same meanings as those of Test 1.

The results were shown in Table 3.

Table 3

| Test Compound | Application rate (g/10 are) | | | |
|---|---|---|---|---|
| | 250 | 125 | 62.5 | 31.3 |
| Compound of Example 1 | — | 5 | 5 | 4 |
| Compound of Example 2 | — | 5 | 5 | 3 |
| Comparative compound | 4 | 1 | 0 | 0 |
| Untreated | | | | 0 |

TEST 4

Post-emergence treatment (foliar treatment)

Seeds of large crab-grass was planted in a pot having 100 square centimeters. When plants became 2 – 4 leaves stage, an aqueous emulsion prepared by diluting an emulsifiable concentrate with water to a specified concentration was sprayed on the foliar of the test plant at a rate of 100 liters per 10 are. The plants were kept in a green house.

21 days after spraying, the degrees of damage to the test plant were observed and estimated by the value of 0 – 5 which have the same meanings as those of Test 1. The results were shown in Table 4.

Table 4

| Test compound | Application rate (g/10a) | | |
|---|---|---|---|
| | 100 | 50 | 25 |
| Compound of Example 1 | 5 | 5 | 5 |
| Compound of Example 2 | 5 | 5 | 4 |
| Comparative compound | | | |
| (structure: OH, NOCH$_2$CH=CH$_2$, C-CH$_3$, pyranone with CH$_3$) | 3 | 2 | 1 |
| (structure: 3,4-dichlorophenyl-NH-C(O)-C$_2$H$_5$) | 3 | 1 | 0 |
| Untreated | | | 0 |

AN EXPLANATION OF THE DRAWING:

FIG. 1 is the infrared spectrum of 3-(1-ethoxyamino-1-hydroxypropyl)-6-ethyl-3,4-dihydro-2H-pyrane-2,4-dione

What is claimed is:

1. A compound of the formula

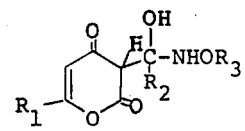

wherein $R_1$ and $R_2$ are alkyl having six or less carbon atoms, $R_3$ is selected from the group consisting of alkyl having six or less carbon atoms and alkenyl having six or less carbon atoms, with the proviso that $R_1$ and $R_2$ do not both represent a methyl group.

2. A compound according to claim 1 in which $R_1$ and $R_2$ are alkyl of 2 to 3 carbon atoms and $R_3$ is selected from the group consisting of alkyl of 2 to 3 carbon atoms and a allyl group.

3. A compound according to claim 1 in which $R_1$, $R_2$ and $R_3$ are an ethyl group.

4. A method for the control of weeds comprising applying a compound of claim 1 in an amount sufficient to exert herbicidal action to a locus to be protected.

5. A method for the control of weeds comprising applying a compound of claim 2 in an amount sufficient to exert herbicidal action to a locus to be protected.

6. A method for the control of weeds comprising applying a compound of claim 3 in an amount sufficient to exert herbicidal action to a locus to be protected.

* * * * *